US008721614B2

(12) United States Patent
Takemoto et al.

(10) Patent No.: US 8,721,614 B2
(45) Date of Patent: May 13, 2014

(54) CONNECTOR ASSEMBLY

(75) Inventors: Masafumi Takemoto, Nakakoma-gun (JP); Takayasu Shimazaki, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 113 days.

(21) Appl. No.: 13/394,680

(22) PCT Filed: Oct. 21, 2010

(86) PCT No.: PCT/JP2010/068628
§ 371 (c)(1),
(2), (4) Date: Mar. 7, 2012

(87) PCT Pub. No.: WO2011/052481
PCT Pub. Date: May 5, 2011

(65) Prior Publication Data
US 2012/0179128 A1  Jul. 12, 2012

(30) Foreign Application Priority Data

Oct. 28, 2009  (JP) ................................. 2009-247329

(51) Int. Cl.
*A61J 1/10* (2006.01)
*A61J 1/20* (2006.01)
*A61M 5/162* (2006.01)
*A61M 39/10* (2006.01)

(52) U.S. Cl.
CPC ............ *A61J 1/20* (2013.01); *A61J 2001/2051* (2013.01); *A61M 5/1626* (2013.01); *A61M 39/10* (2013.01); *A61M 39/1011* (2013.01); *A61M 2039/1072* (2013.01); *A61J 1/2089* (2013.01); *A61J 2001/2055* (2013.01); *A61J 2001/2065* (2013.01); *A61M 2039/1066* (2013.01)
USPC ........... 604/414; 604/403; 604/408; 604/411; 604/412; 604/413

(58) Field of Classification Search
CPC ......... A61J 1/20; A61J 1/2089; A61J 1/2093; A61J 1/2096; A61J 2001/2051; A61J 2001/2055; A61J 2001/2065; A61M 5/162; A61M 5/1626; A61M 39/10; A61M 39/1011; A61M 2039/10; A61M 2039/1044; A61M 2039/1066; A61M 2039/1072
USPC ......... 604/403, 408, 411, 412, 413, 414, 415, 604/416
See application file for complete search history.

(56) References Cited

U.S. PATENT DOCUMENTS 4,576,211 A * 3/1986 Valentini et al. .............. 141/329
(Continued)

FOREIGN PATENT DOCUMENTS

JP            6-042675 Y2      11/1994
(Continued)

OTHER PUBLICATIONS

International Search Report (PCT/ISA/210) issued on Nov. 22, 2010, by Japanese Patent Office as the International Searching Authority for International Application No. PCT/JP2010/068628.
(Continued)

*Primary Examiner* — Adam Marcetich
(74) *Attorney, Agent, or Firm* — Buchanan Ingersoll & Rooney PC

(57) ABSTRACT

A connector assembly includes a first connector having a tubular first connector body, a hollow needle inside the first connector body and a first sealing component piercable by the needle, and a second connector having a tubular second connector body and a second sealing component. The second sealing component is in the second connector body, is attached to a first piercing section when inserted into the first connector body, and, in that state, is pierced by the needle together with the first piercing section. The connector assembly also includes a restriction which, when the second connector is inserted into the first connector, temporarily interrupts and restricts the insertion operation, but allows resumption of such operation when the restriction is removed, and which, when the second connector is withdrawn from the first connector, temporarily interrupts and restricts the withdrawing operation, but allows such operation to resume when the restriction is removed.

7 Claims, 13 Drawing Sheets

(56) References Cited

U.S. PATENT DOCUMENTS

| | | | | |
|---|---|---|---|---|
| 4,872,494 A | * | 10/1989 | Coccia | 141/383 |
| 4,895,570 A | * | 1/1990 | Larkin | 604/411 |
| 5,279,597 A | * | 1/1994 | Dassa et al. | 604/535 |
| 5,374,088 A | * | 12/1994 | Moretti et al. | 285/305 |
| 5,647,845 A | * | 7/1997 | Haber et al. | 604/32 |
| 6,022,339 A | | 2/2000 | Fowles et al. | |
| 2003/0199847 A1 | | 10/2003 | Akerlund et al. | |
| 2006/0276770 A1 | * | 12/2006 | Rogers | 604/414 |
| 2007/0029796 A1 | * | 2/2007 | Bibby | 285/308 |
| 2008/0306424 A1 | * | 12/2008 | Gallogly et al. | 604/6.1 |
| 2009/0069783 A1 | * | 3/2009 | Ellstrom et al. | 604/415 |
| 2011/0074148 A1 | | 3/2011 | Imai | |
| 2011/0106046 A1 | * | 5/2011 | Hiranuma et al. | 604/414 |

FOREIGN PATENT DOCUMENTS

| | | |
|---|---|---|
| JP | 2002-524217 A | 8/2002 |
| JP | 2005-522282 A | 7/2005 |
| WO | WO 2009/133754 A1 | 11/2009 |

OTHER PUBLICATIONS

Written Opinion (PCT/ISA/237) issued on Nov. 22, 2010, by Japanese Patent Office as the International Searching Authority for International Application No. PCT/JP2010/068628.

\* cited by examiner

CONNECTOR ASSEMBLY

TECHNICAL FIELD

The present invention relates to a connector assembly.

BACKGROUND ART

Normally, a drug which is dangerous if a medical care worker touches it by mistake, such as carcinostatics, immunosuppressants, etc. is contained in a powdery state in a vial container having a mouth part sealed with a rubber plug.

At the time of taking the drug out of such a vial container, the following operations are performed.

First, the mouth part of the vial container and a spout of a syringe into which dissolving liquid has been portioned out are connected to each other through a connector (see Patent Document 1). Next, in this connected condition, the dissolving liquid is injected from the syringe into the vial container. Then, by such an operation as a pumping operation, shaking of the vial container, or the like, the drug is dissolved uniformly in the dissolving liquid. Subsequently, the dissolving liquid with the drug dissolved therein (hereinafter, referred to as "liquid medical agent") is taken out into the syringe by suction.

The connector disclosed in Patent Document 1 that is used for such operations includes a hollow needle having a sharp needle point at its distal end, a hub for supporting the hollow needle, and a cover member for covering the needle point. The cover member can be moved along the longitudinal direction of the hollow needle, and can be displaced into a first position for covering the needle point and a second position for letting the needle point exposed. In addition, this connector has a stopper for inhibiting the cover member from being unwillingly moved from the first position to the second position. The connector having such a constitution can be used in a state (hereinafter referred to as "use condition") wherein, for example, the hub is connected to the syringe, and the stopper is operated to put the cover member into the second position, and the rubber plug of the vial container is punctured by the hollow needle. In the use condition, the inside of the syringe and the inside of the vial container communicate with each other through the connector (hollow needle).

However, in the connector disclosed in Patent Document 1, if such force as to pull the hollow needle from the rubber plug of the vial container acts in the use condition, then the hollow needle would be easily pulled out of the rubber plug of the vial container. In this case, the liquid medical agent may be scattered from the exposed needle point, and adhere to a medical care worker or the like, or the medical care worker may be punctured with the needle point by mistake. Thus, there has been a problem that it is impossible to transfer the liquid medical agent through the connector safely and reliably.

Patent Document 1: Japanese Laid-Open Patent Publication No. 2005-522282 (PCT)

SUMMARY OF INVENTION

It is an object of the present invention to provide a connector assembly which is capable of transferring liquid safely and reliably from a first connector side to a second connector side or in the opposite direction.

In order to attain the above object, the present invention provides a connector assembly which includes a first connector, and a second connector for being inserted in the first connector, the first connector including a tubular first connector body provided at a distal end thereof with an opening for insertion of the second connector and at a proximal end thereof with a first connection section for connection with a first medical instrument, a hollow needle provided in an inner cavity section of the first connector body so as to communicate with the first connection section and which is provided with an opening part opening at a distal end portion thereof, a first sealing member for sealing the inner cavity section of the first connector body and which is made of an elastic material, the first sealing member having a first puncture section capable of being punctured by the hollow needle, and a biasing member for biasing the first puncture section in a distal end direction, and the second connector including a tubular second connector body provided at a distal end thereof with a second connection section for connection with a second medical instrument, and a second sealing member for sealing an inner cavity section of the second connector body and which is made of an elastic material and provided at a proximal end of the second connector body, the second sealing member having a second puncture section which makes close contact with the first puncture section when the second connector is inserted in the first connector body, wherein the first connector is provided with operation restricting means which, when the second connector is inserted into the first connector, temporarily restricts the insertion operation and permits resumption of the insertion operation if the restriction is released, and which, when the second connector is withdrawn from the first connector, temporarily restricts the withdrawing operation and permits resumption of the withdrawing operation if the restriction is released;

in the process of insertion of the second connector into the first connector, the insertion operation is temporarily restricted by the operation restricting means when the first puncture section and the second puncture section make close contact with each other, and, upon resumption of the insertion operation by releasing the restriction, the first puncture section and the second puncture section in the close contact state are punctured by the hollow needle, and the opening part of the hollow needle is located on the distal end side relative to the second puncture section and then exposed to the inside of the inner cavity section of the second connector body; and in the process of withdrawal of the second connector from the first connector, the withdrawing operation is temporarily restricted by the operation restricting means when the opening part of the hollow needle is located on the proximal end side relative to the first puncture section in the close contact state, and, upon resumption of the withdrawing operation by releasing the restriction, the first puncture section and the second puncture section are separated away from each other.

In addition, in the connector assembly according to the present invention, preferably, the first connector has a biasing member for biasing the first puncture section in a distal end direction.

Further, the connector assembly according to the invention, preferably, further includes locking means for locking the close contact state of the first puncture section and the second puncture section in conjunction with a releasing operation of releasing the restriction on the insertion operation.

In addition, in the connector assembly according to the invention, preferably, the first connector body includes an outer tube, and an inner tube displaceably disposed inside the outer tube; and the locking means includes a plurality of engagement pieces disposed on the inner tube around an axis of the inner tube and being elastic, a pressing part provided on the outer tube and operative to press the engagement pieces against elastic force of the engagement pieces, and an engagement section provided on the second connector body and operative to engage with each of the engagement pieces when each of the engagement pieces is pressed by the pressing part.

Further, in the connector assembly according to the invention, preferably, the first connector body includes an outer tube, and an inner tube displaceably disposed inside the outer tube; and the operation restricting means includes a groove part which has a transverse groove formed in a wall part of one of the outer tube and the inner tube along a circumferential direction of the wall part and a longitudinal groove formed in the wall part along an axial direction of the wall part and communicating with the transverse groove, and a projected section which projects from a wall part of the other of the outer tube and the inner tube so as to be inserted in the groove part and which is moved in the groove part in accordance with displacement of the inner tube, and restriction on the insertion operation and release of the restriction and restriction on the withdrawing operation and release of the restriction can be performed depending on a position of the projected section in the groove part.

In addition, in the connector assembly according to the invention, preferably, the first connector body is provided with a stopper for restricting movement of the second connector body in the distal end direction in conjunction with the insertion operation.

Further, in the connector assembly according to the invention, preferably, the stopper includes a first engagement section provided on the outer tube, an elastic section for biasing the first engagement section toward the inside of the outer tube, and a plurality of second engagement sections which are provided on the second connector body and which engage with the first engagement section depending on depth of insertion of the second connector body into the first connector.

In addition, in the connector assembly according to the invention, preferably, the release of the restriction on the insertion operation and the release of the restriction on the withdrawing operation are performed by relative rotation of the first connector and the second connector around the axis, and, at that time, the first puncture section and the second puncture section are rotated in the same direction.

Additionally, in the connector assembly according to the invention, preferably, the first medical instrument has a syringe outer tube; and In the first connector, the first connection section thereof is connected to a spout of the syringe outer tube.

In addition, in the connector assembly according to the invention, preferably, the second medical instrument has a liquid container capable of containing a liquid therein; and In the second connector, the second connection section thereof is connected to a mouth part of the liquid container.

Further, in the connector assembly according to the invention, preferably, the first puncture section and the second puncture section are each plate-like in shape and are each disposed such that the thickness direction thereof coincides with the axial direction.

In addition, in the connector assembly according to the invention, preferably, at least one of the first puncture section and the second puncture section is formed at an end surface thereof with a protuberant part which is flattened in a close contact state.

Further, in the connector assembly according to the invention, preferably, the sliding resistance between the hollow needle and the first puncture section at the time of withdrawal of the second connector from the first connector is smaller than the biasing force of the biasing member.

DESCRIPTION OF EMBODIMENTS

Now, a connector assembly according to the present invention will be described in detail below, based on preferred embodiments shown in the accompanying drawings.

Figure 1:
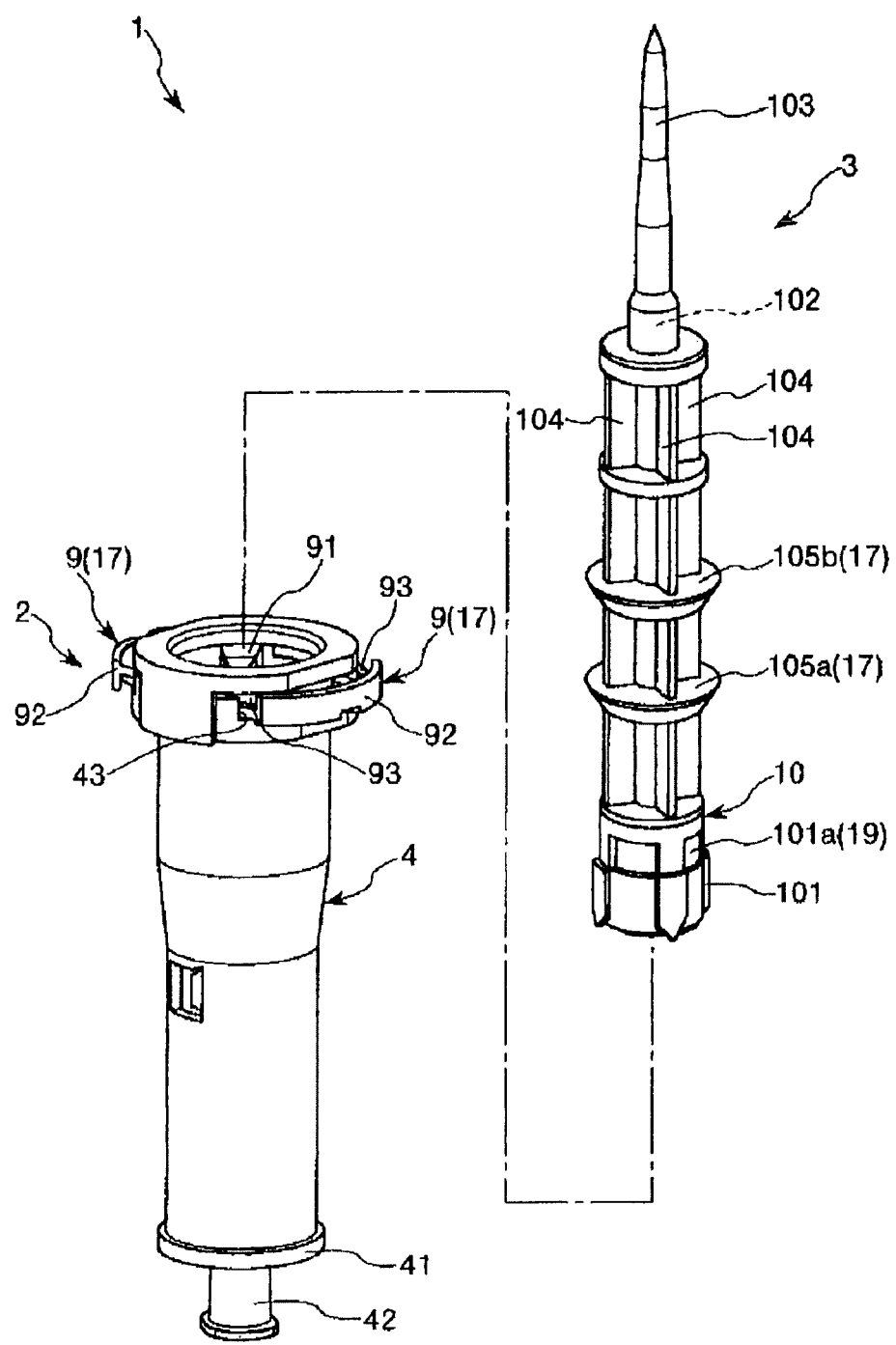
FIG. 1 is an exploded perspective view of an embodiment of a connector assembly according to the present invention.
Figure 10:
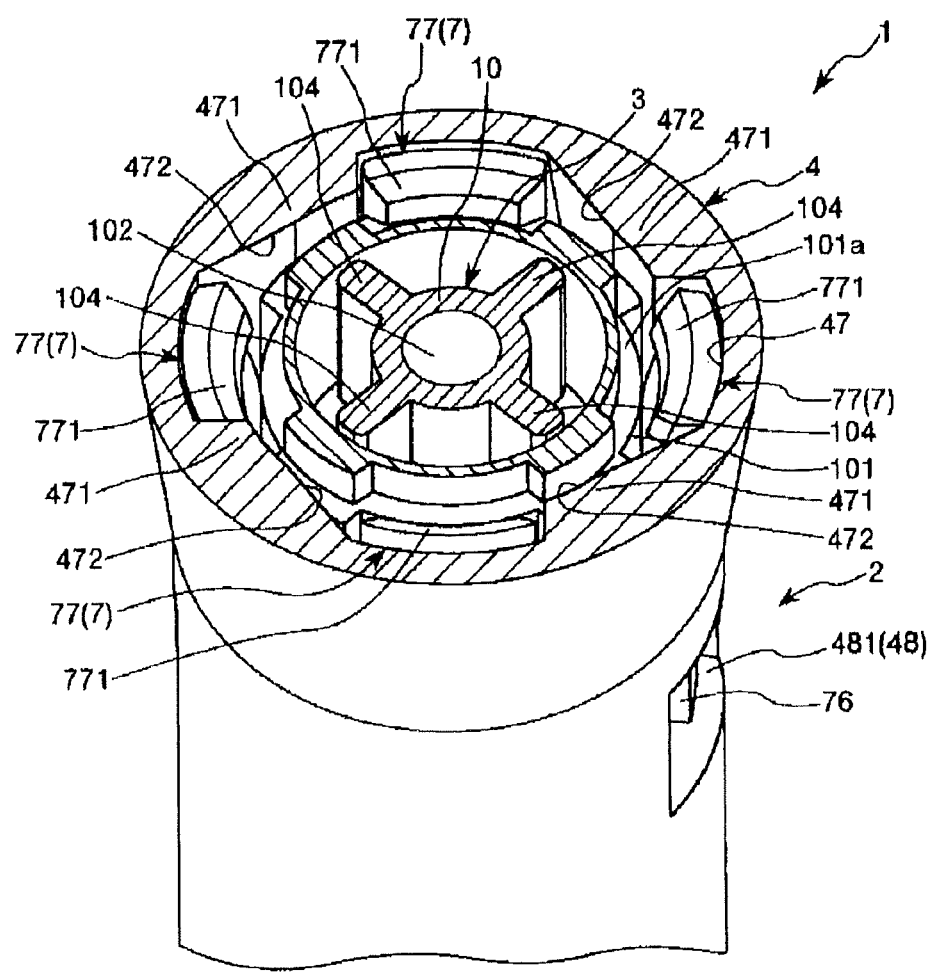
FIG. 10 is a sectional view taken along line A-A of FIG. 3.
Figure 11:
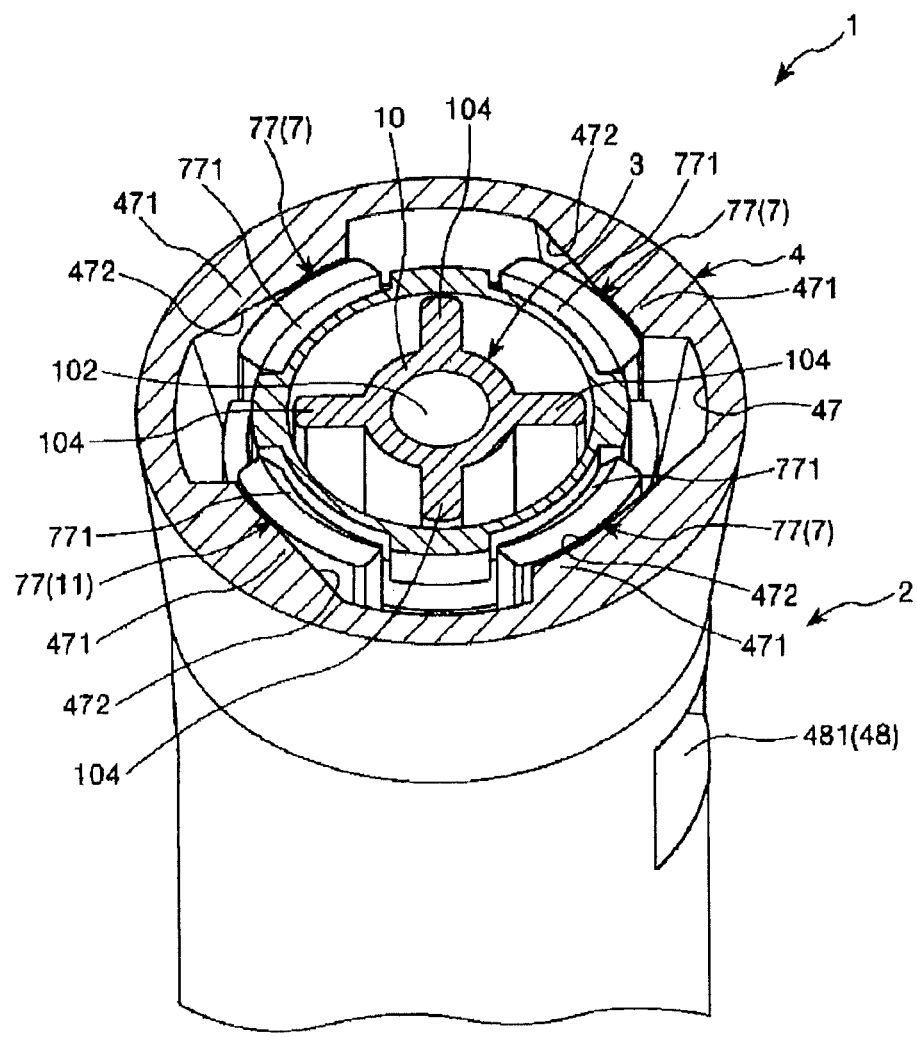
FIG. 11 is a sectional view taken along line B-B of FIG. 4.
Figure 12:
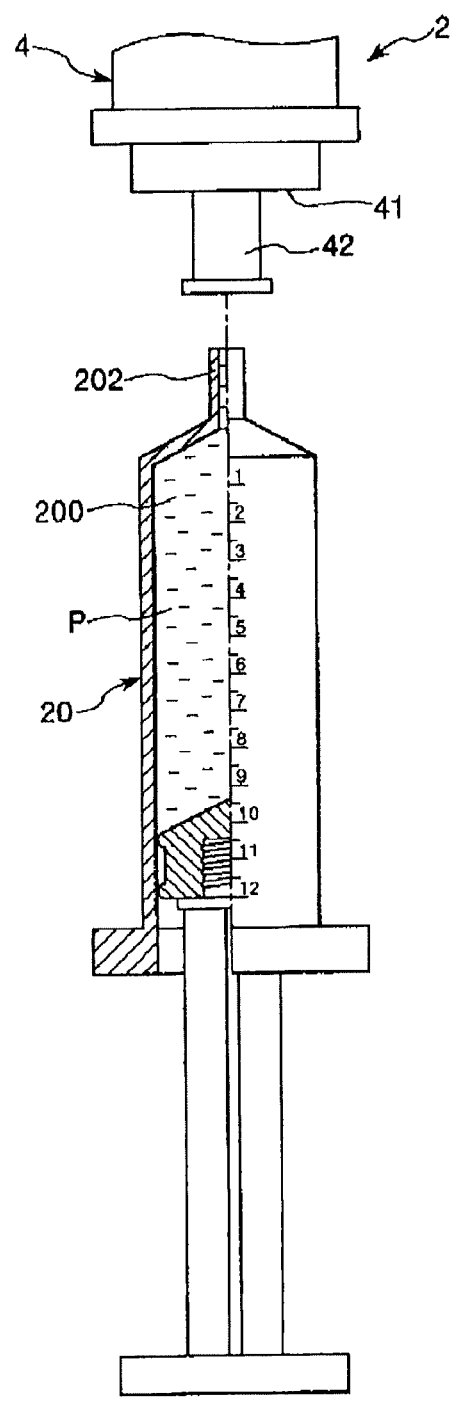
FIG. 12 is a partial longitudinal sectional view of a syringe to be connected to the first connector of the connector assembly shown in FIG. 1.
Figure 13:
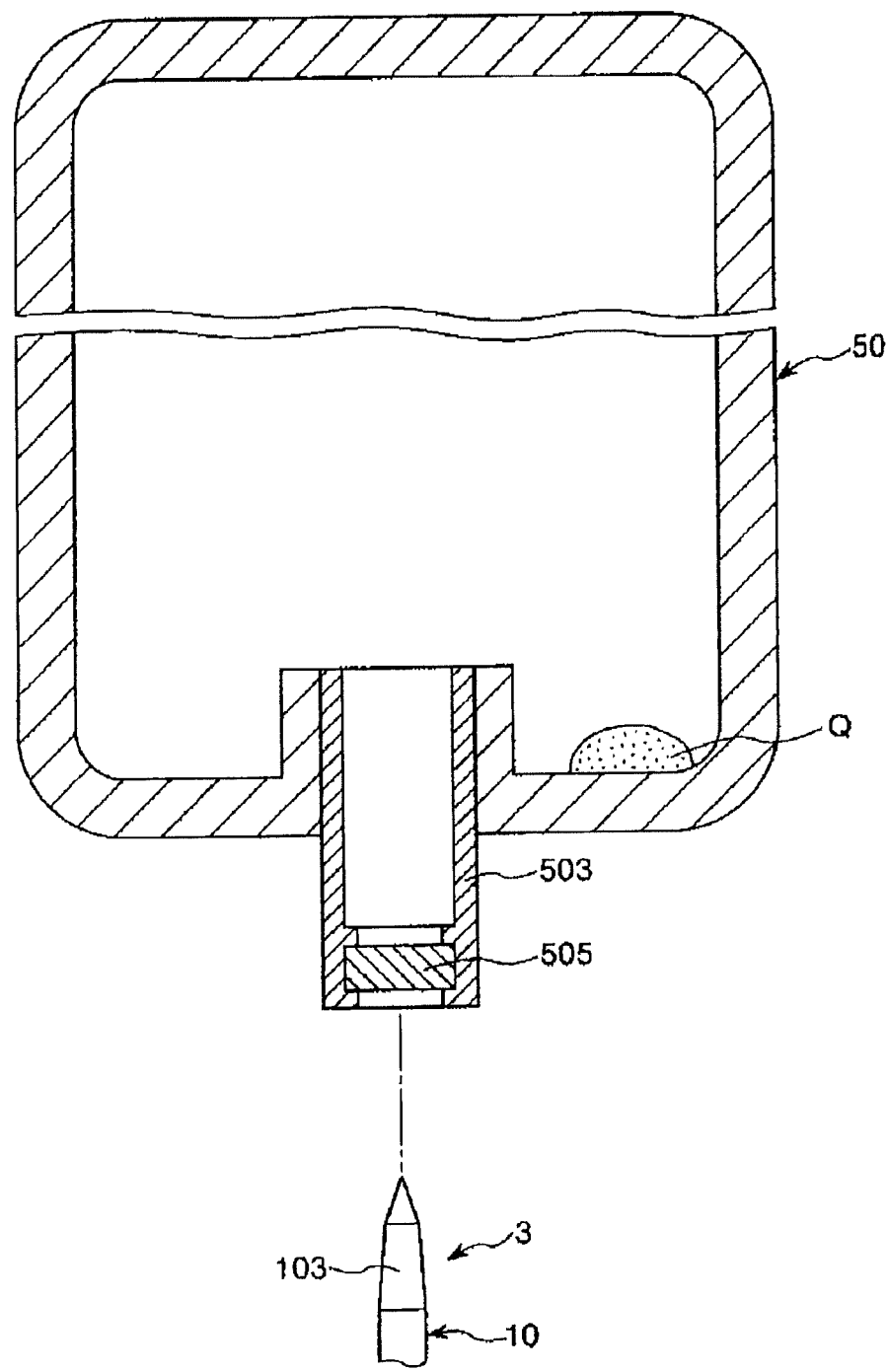
FIG. 13 is a longitudinal sectional view of a bag to be connected to the second connector of the connector assembly shown in FIG. 1.

FIG. 1 is an exploded perspective view showing an embodiment of the connector assembly of the present invention; FIGS. 2 to 5 are longitudinal sectional views illustrating a process in which a first connector and a second connector of the connector assembly shown in FIG. 1 are brought into an assembled state; FIGS. 6 to 9 are perspective views (views corresponding respectively to FIGS. 2 to 5) illustrating the process in which the first connector and the second connector of the connector assembly shown in FIG. 1 are brought into the assembled state; FIG. 10 is a sectional view taken along line A-A of FIG. 3; FIG. 11 is a sectional view taken along line B-B of FIG. 4; FIG. 12 is a partial longitudinal sectional view of a syringe to be connected to the first connector of the connector assembly shown in FIG. 1; and FIG. 13 is a longitudinal sectional view of a bag to be connected to the second connector of the connector assembly shown in FIG. 1. Incidentally, in the following, for convenience of description, the upper side in FIGS. 1 to 13 will be referred to as "distal end," "upper" or "upper side," and the lower side as "proximal end," "lower" or "lower side."

As shown in FIGS. 1 to 9, a connector assembly 1 includes a first connector (female connector) 2 and a second connector (male connector) 3. As shown in FIG. 12, the first connector 2 is mounted to a syringe (first medical instrument) 20. As shown in FIG. 13, the second connector 3 is mounted to a bag (second medical instrument) 50. The connector assembly 1, in an assembled state (the state shown in FIGS. 5 and 9) in which the second connector 3 has been inserted into the first connector 2 from the distal end side thereof to assemble the connectors onto each other, is used for transferring a liquid from the first connector 2 side to the second connector 3 side or in the opposite direction.

The bag 50 contains therein a powdery drug Q. The bag 50 is provided at a proximal end portion thereof with a mouth part 503 composed of a hard pipe. Through the mouth part 503, a liquid can flow into and out of the bag 50.

Further, a rubber plug 505 for sealing the mouth part 503 is mounted to the mouth part 503. The rubber plug 505 is pierced by a bottle needle section 103 of the second connector 3. In the pierced condition, the second connector 3 and the bag 50 communicate with each other.

Although the drug Q to be contained in the bag 50 is not particularly limited, the drug Q includes a drug which is dangerous if a medical care worker touches it by mistake, such as carcinostatics, immunosuppressants, etc., a drug which requires dissolution before use, such as an antibiotic, a hemostatic, etc., a drug which requires dilution, such as pediatric medical agents, a drug to be used over a plurality of times, such as vaccine, heparin, pediatric medical agents, etc. In addition, the drug Q is not limited to a powdery drug but may be, for example, a liquid drug.

Now, the connector assembly 1 will be described below. As above-mentioned, the connector assembly 1 has the first connector 2 and the second connector 3.

As shown in FIGS. 2 to 5, the first connector 2 includes a first connector body having an outer tube 4 and an inner tube 7 which are cylindrical, a hollow needle 5 supported by the outer tube 4, a first sealing member 6 supported by the inner tube 7, a coil spring 8 serving as a biasing member for biasing the first sealing member 6 in the distal end direction, and a clamping member 9 disposed on the outer tube 4.

Figure 2:
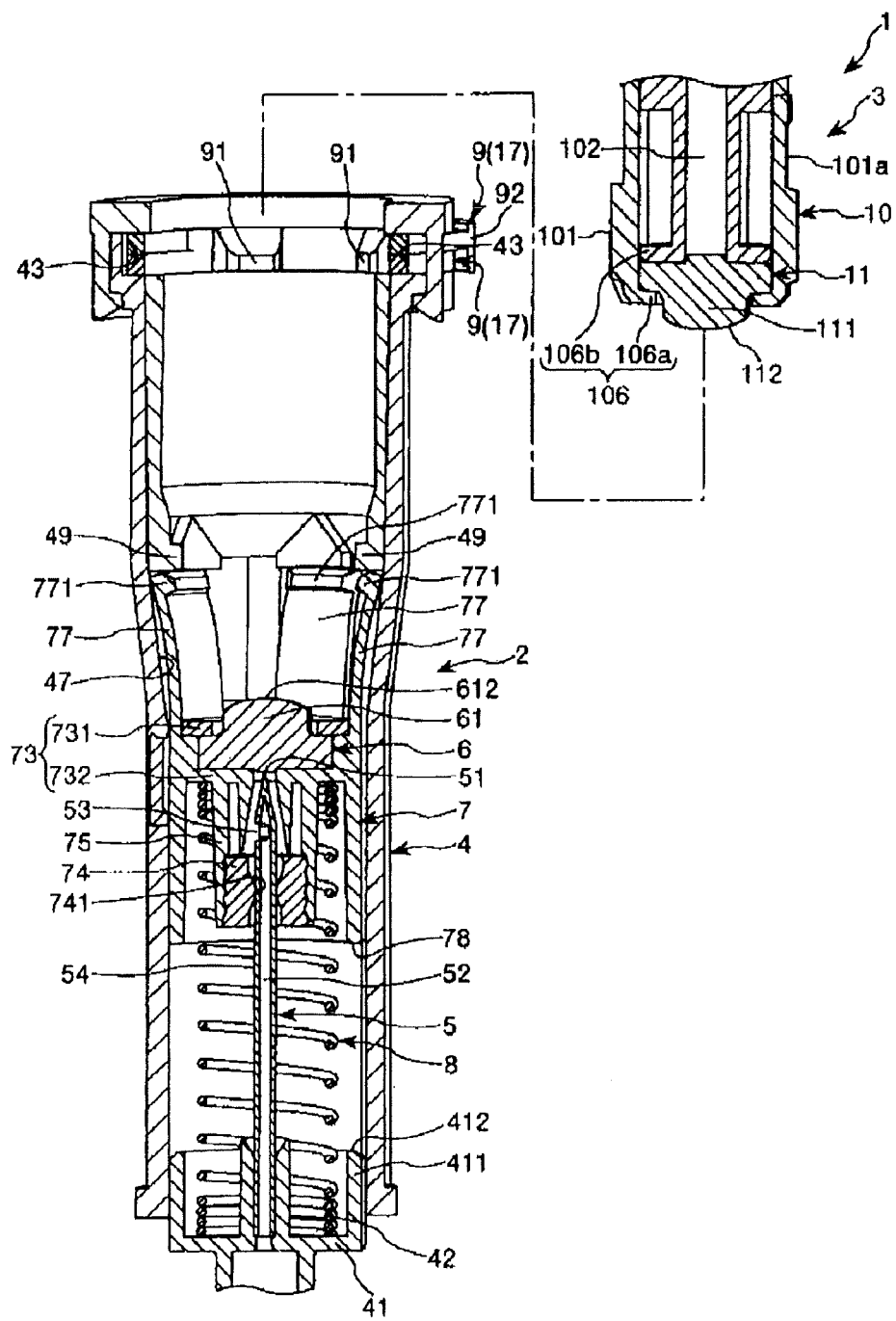
FIG. 2 is a longitudinal sectional view showing a process in which a first connector and a second connector of the connector assembly shown in FIG. 1 are brought into an assembled state.

As shown in FIGS. 1 and 2, the outer tube 4 is in the shape of a bottomed tube. The second connector 3 is inserted into the outer tube 4 via a distal end opening of the outer tube 4.

In addition, at a central portion of a bottom section 41 of the outer tube 4, a tubular hub part 42 is formed concentrically with the outer tube 4. The hub part 42 can support a proximal end portion of the hollow needle 5 at a distal end portion thereof. Owing thereto, the hub part 42 and the hollow needle 5 communicate with each other. In addition, into a proximal end portion (first connection section) of the hub part 42, a spout 202 of the syringe 20 can be inserted (connected) (see FIG. 12). As a result, the first connector 2 is attached to the syringe 20, and, in this attached condition, the first connector 2 can be used. In addition, in the attached condition, a space 200 in the syringe 20 and an inner cavity (first passage 52) of the hollow needle 5 communicate with each other via the hub part 42. Owing thereto, a dissolving liquid P can be supplied from the syringe 20 into the hollow needle 5.

As shown in FIGS. 6 to 9, a wall part of the outer tube 4 is provided at an intermediate portion thereof with a groove part 48 penetrating the wall part. The groove part 48 is in the shape of letter "L" as viewed from the side and is composed of a transverse groove 481 formed in the circumferential direction of the wall part of the outer tube 4, and a longitudinal groove 482 formed along the axial direction of the outer tube 4 from one end of the transverse groove 481 toward the proximal end side. A projected part 76 of the inner tube 7 is inserted in the groove part 48. Then, the projected part 76 of the inner tube 7 can be moved within the groove part 48.

As shown in FIGS. 2 to 5, the wall part of the outer tube 4 is provided at a distal end portion thereof with a pair of groove parts 43, which face each other across the center axis of the outer tube 4. In the groove part 43, two ring-shaped clamping members 9 are inserted in a stacked state. The clamping members 9 function as a part of a stopper 17 which restricts movement of the second connector 3 (the second connector body 10) in the distal end direction in the outer tube 4. As the constitution of the stopper 17, known constitutions (for example, the constitution of the "hub attachment/detachment mechanism" disclosed in Japanese Laid-Open Patent Publication No. 08-126630) can be used.

In this case, each of the clamping members 9 is provided at a part of an outer peripheral portion thereof with an operating section 92 operated to press the clamping member 9. With the operating section 92 pressed, the clamping member 9 is moved in a direction perpendicular to the axis of the outer tube 4.

In addition, each of the clamping members 9 is provided, at a part on the opposite side to the operating section 92, with a plurality of projected parts (first engagement section) 91 projected toward the inside. Further, the projected parts 91 of the clamping member 9 on one side and the projected parts 91 of the clamping member 9 on the other side are arranged so as to face each other across the center axis of the outer tube 4.

Further, each of the clamping members 9 is provided, on the same side as the projected parts 91, with a pair of elastic pieces 93 projected from an outer peripheral portion thereof. The elastic pieces 93 of the clamping member 9 on one side abut on the inside of the operating section 92 of the clamping member 9 on the other side, and, similarly, the elastic pieces 93 of the clamping member 9 on the other side abut on the inside of the operating section 92 of the clamping member 9 on the one side.

At the time of pressing each of the clamping members 9, the pressing operation is conducted against the biasing force (elastic force) of the elastic pieces 93. By this operation, the projected parts 91 of the clamping member 9 on one side and the projected parts 91 of the clamping member 9 on the other side are separated away from each other. When the pressing force on the clamping members 9 is removed, the biasing force of the elastic pieces 93 causes the projected parts 91 of the clamping member 9 on one side and the projected parts 91 of the clamping member 9 on the other side to approach each other.

Figure 3:
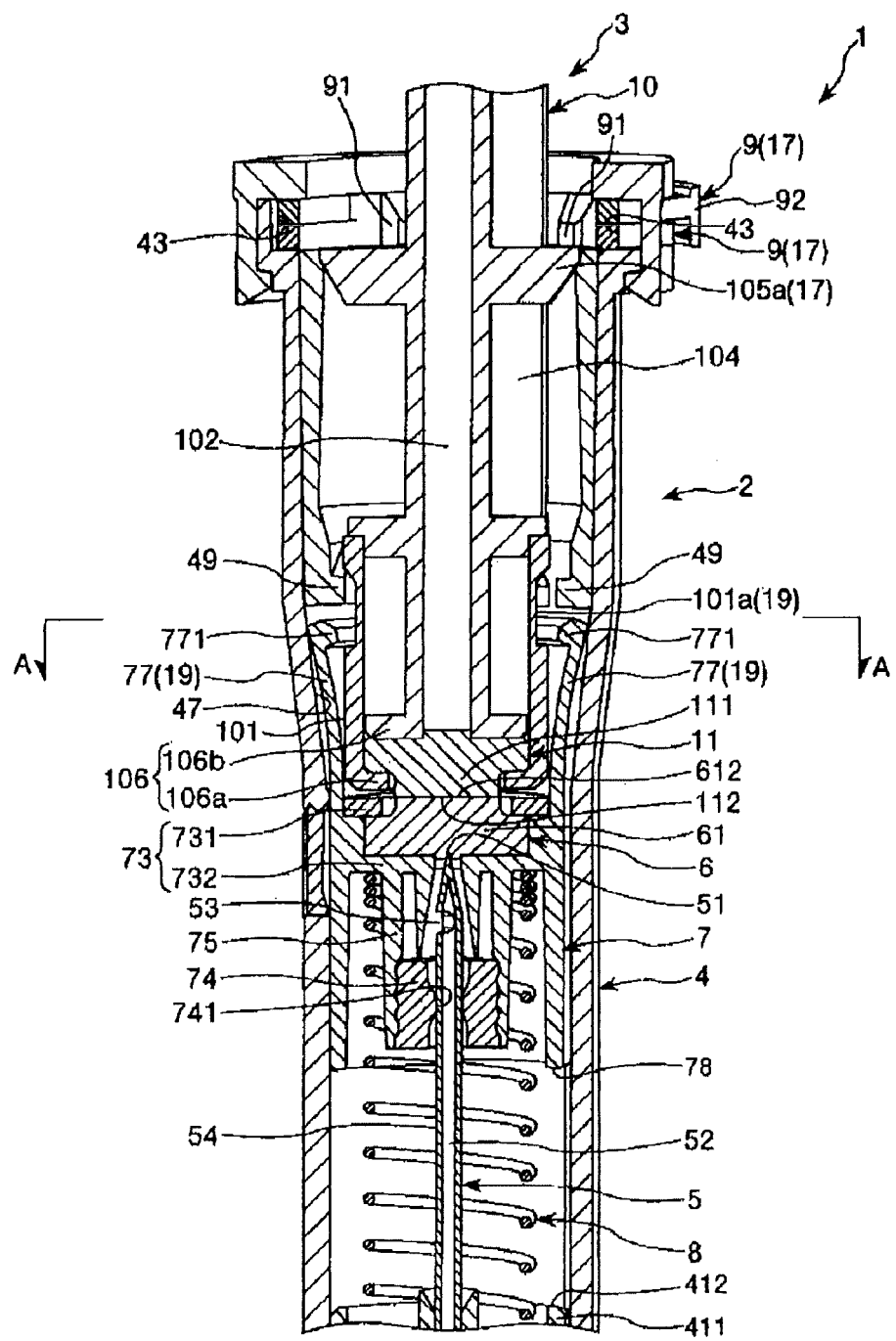
FIG. 3 is a longitudinal sectional view showing the process in which the first connector and the second connector of the connector assembly shown in FIG. 1 are brought into the assembled state.
Figure 4:
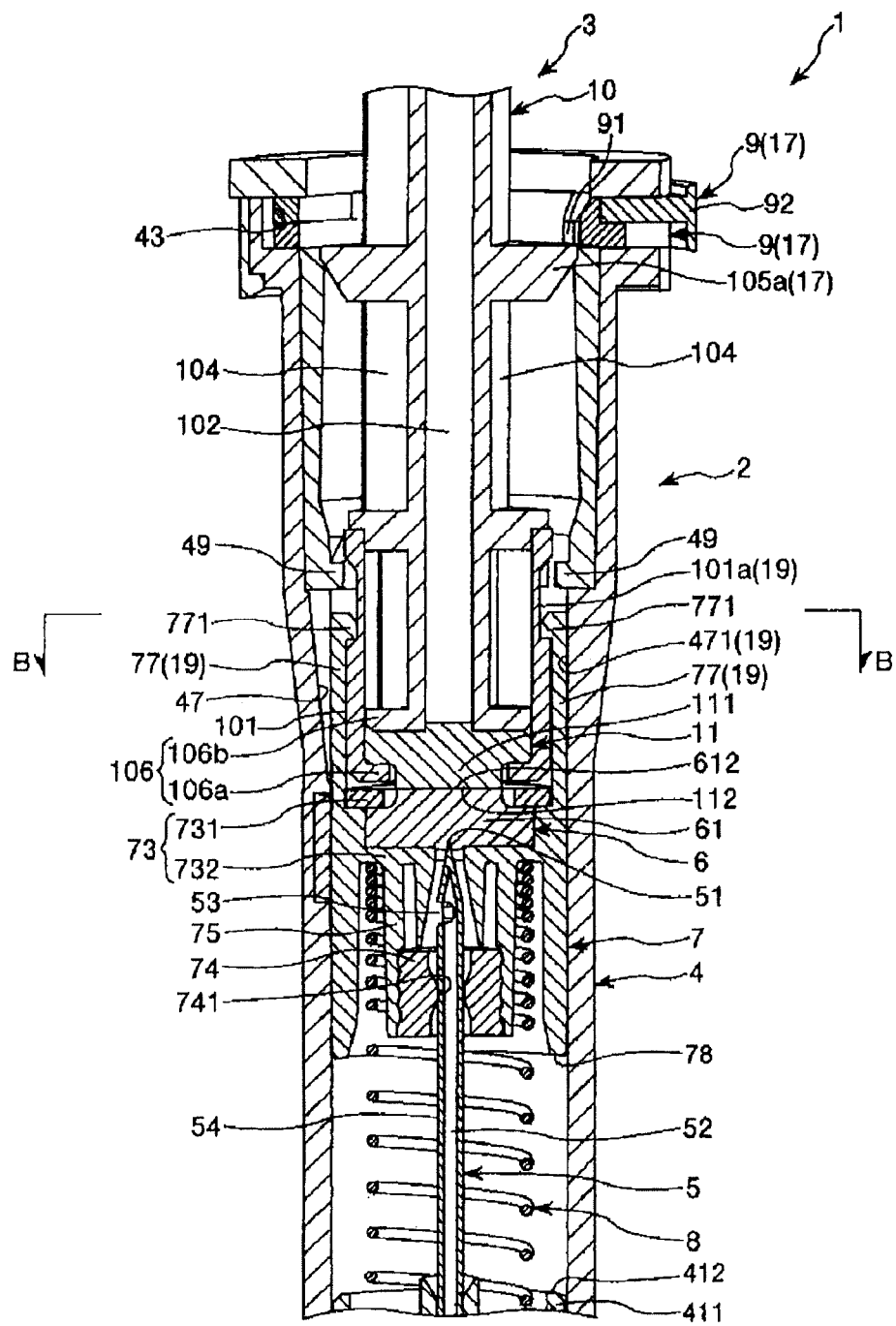
FIG. 4 is a longitudinal sectional view showing the process in which the first connector and the second connector of the connector assembly shown in FIG. 1 are brought into the assembled state.
Figure 5:
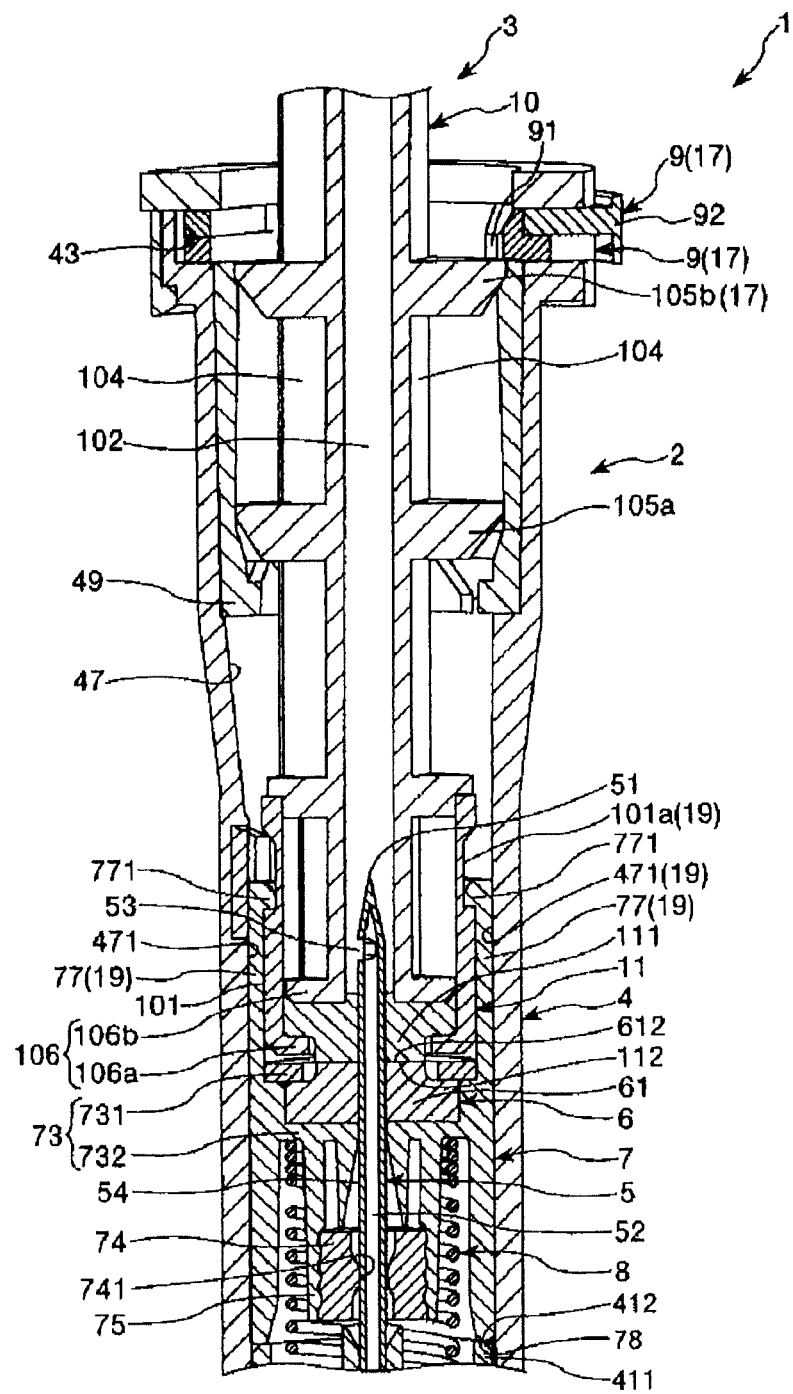
FIG. 5 is a longitudinal sectional view showing the process in which the first connector and the second connector of the connector assembly shown in FIG. 1 are brought into the assembled state.

In the condition where the projected parts 91 of the clamping member 9 on one side and the projected parts 91 of the clamping member 9 on the other side are close to each other, the projected parts 91 are collectively engaged with an engagement section (second engagement section) 105a or 105b of the second connector 3 (see FIGS. 3 to 5). This ensures that the second connector 3 can be reliably prevented from being unwillingly disengaged from the outer tube 4.

On the other hand, in the condition where the projected parts 91 of the clamping member 9 on one side and the projected parts 91 of the clamping member 9 on the other side are separated away from each other, the clamping members 9 and the second connector 3 are disengaged from each other.

As shown in FIG. 1, the engagement sections 105a and 105b of the second connector 3 are each composed of a flange section which is formed on an outer peripheral portion of the second connector body 10 and which has an enlarged outside diameter. The engagement sections 105a and 105b are arranged at an interval along the axial direction of the second connector body 10. As shown in FIGS. 3 and 5, the engagement section 105a or 105b engages with the projected parts 91 as above-mentioned, depending on the depth of insertion of the second connector 3 into the first connector.

In the connector assembly 1, it can be said that the clamping members 9 and the engagement sections 105a and 105b of the second connector 3 jointly form the "stopper 17" by which the outer tube 4 and the second connector 3 are locked together.

Figure 6:
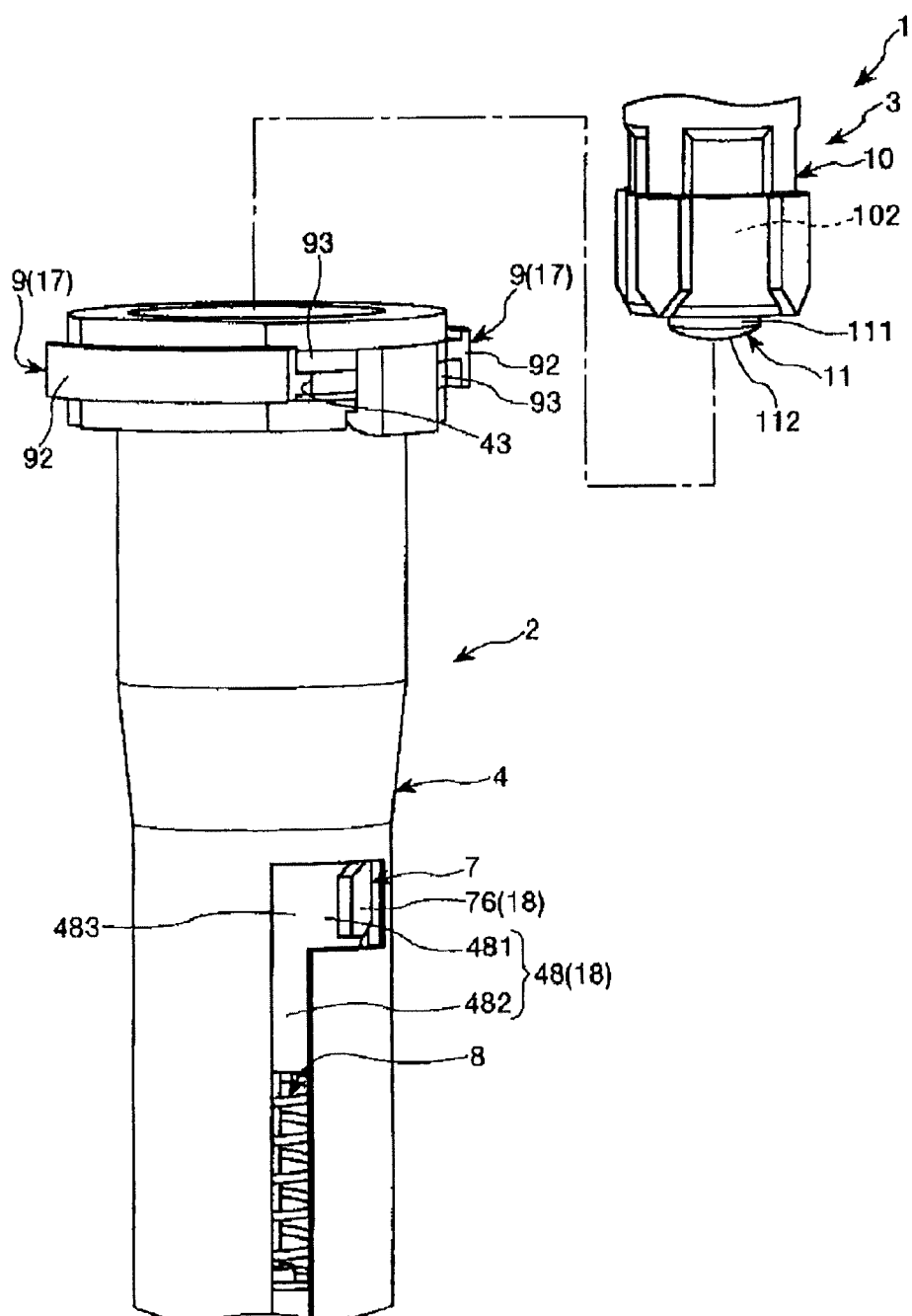
FIG. 6 is a perspective view (a view corresponding to FIG. 2) showing the process in which the first connector and the second connector of the connector assembly shown in FIG. 1 are brought into the assembled state.

As shown in FIGS. 2 and 6, the wall part of the outer tube 4 is formed, at a portion of an inner peripheral portion 47 thereof between the groove part 48 and the groove parts 43, with a plurality of (four in this embodiment) stepped parts 49 projected toward the inside. As shown in FIG. 2, the inner tube 7 abuts on the stepped parts 49, whereby movement of the inner tube 7 in the distal end direction can be restricted, and, therefore, the inner tube 7 can be reliably prevented from being disengaged from the outer tube 4.

As shown in FIG. 2 (and also in FIGS. 3 to 5), the inner tube 7 is disposed (supported) inside the outer tube 4. The inner tube 7 is displaceable relative to the outer tube 4; more specifically, the inner tube 7 is rotatable about the axis of the outer tube 4 and is movable along the axial direction of the outer tube 4.

The inner tube 7 has a sealing member mounting section 73 where to mount the first sealing member 6. The sealing member mounting section 73 is composed of a pair of annular plate-shaped sections 731 and 732 which are provided on the inside of the inner tube 7 and which vertically sandwich the first sealing member 6 therebetween.

In addition, the inner tube 7 has a sliding member 74 which slides the hollow needle 5 when the inner tube 7 is displaced, and a fixing section 75 which fixes the sliding member 74. The sliding member 74 is a tubular member which is formed from an elastic material and has a reduced diameter part 741 having a reduced inner diameter. The material for the sliding member 74 is not particularly limited. Examples of the material include elastic materials such as various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin, styrene or the like, and their mixtures, etc. When the inner tube 7 is displaced, the reduced diameter part 741 slides while being kept in abutment with an outer peripheral portion 54 of the hollow needle 5. The fixing section 75 is a tubular part formed integrally with the plate-shaped section 732 so as to project downwardly.

As shown in FIG. 6 (and also in FIGS. 7 to 9), a wall part of the inner tube 7 has a projected part 76 projectingly formed on an outer peripheral portion thereof. The projected part 76 is inserted in the groove part 48 of the outer tube 4, and is moved within the groove part 48 in accordance with displacement of the inner tube 7. Owing thereto, the first connector 2 can be brought into a first state (the state shown in FIGS. 6 and 7) in which the projected part 76 is located in the transverse groove 481, a second state (the state shown in FIG. 8) in which the projected part 76 is located at an intersection part 483 of the transverse groove 481 and the longitudinal groove 482 as a result of rotating the inner tube 7 relative to the outer tube 4 starting from the first state, and a third state (the state shown in FIG. 9) in which the projected part 76 is located in the longitudinal groove 482 as a result of pushing the inner tube 7 downwardly relative to the outer tube 4 starting from the second state.

When the second connector 3 is inserted into the first connector 2 being in the first state shown in FIG. 6 (FIG. 2) (this operation will hereinafter be referred to as the "insertion operation"), the second sealing member 11 of the second connector 3 is brought into abutment with the first sealing member 6 of the first connector 2, thereby to press the first sealing member 6 in the proximal end direction for trying to move the first sealing member 6 together with the inner tube 7. However, since the projected part 76 of the inner tube 7 is located in the transverse groove 481 of the outer tube 4, the movement of the inner tube 7 in the proximal end direction is restricted (see FIGS. 3 and 7).

Figure 7:
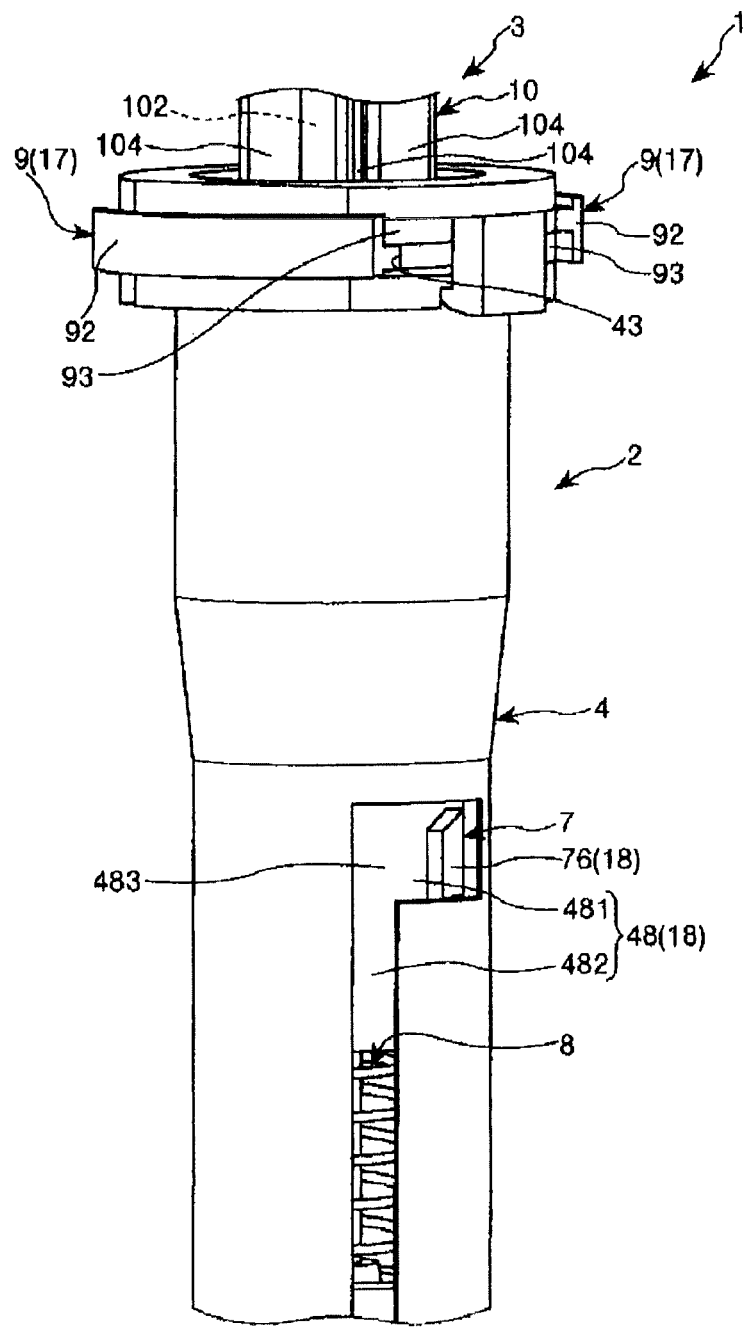
FIG. 7 is a perspective view (a view corresponding to FIG. 3) showing the process in which the first connector and the second connector of the connector assembly shown in FIG. 1 are brought into the assembled state.
Figure 8:
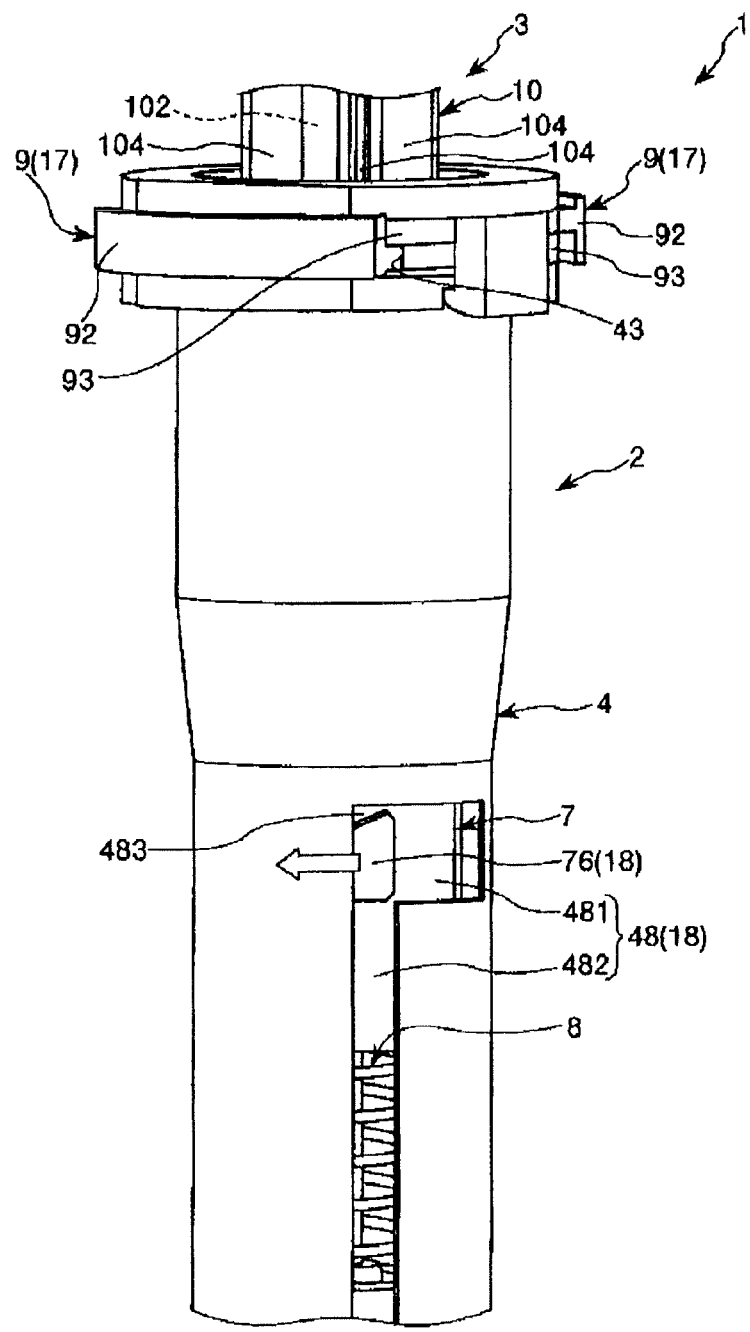
FIG. 8 is a perspective view (a view corresponding to FIG. 4) showing the process in which the first connector and the second connector of the connector assembly shown in FIG. 1 are brought into the assembled state.

When, for example, a finger is put on the projected part 76 of the inner tube 7 and the inner tube 7 is rotated in the direction of arrow in FIG. 8 from the condition shown in FIG. 7, the first connector 2 is brought into the second state shown in FIG. 8. By this operation, the restriction on movement of the inner tube 7 in the proximal end direction is released, thereby to enable the movement in the proximal end direction, so that the insertion operation can be resumed. Incidentally, as shown in FIG. 4, even in the second state, the close contact between the first sealing member 6 and the second sealing member 11 is maintained. Further, in the second state, the inner tube 7 and the second connector 3 (second connector body 10) are locked (connected) to each other by locking means 19. This ensures that close contact between a first puncture section 61 of the first sealing member 6 and a second puncture section 111 of the second sealing member 11 is fixed. The locking means 19 will be described later.

Figure 9:
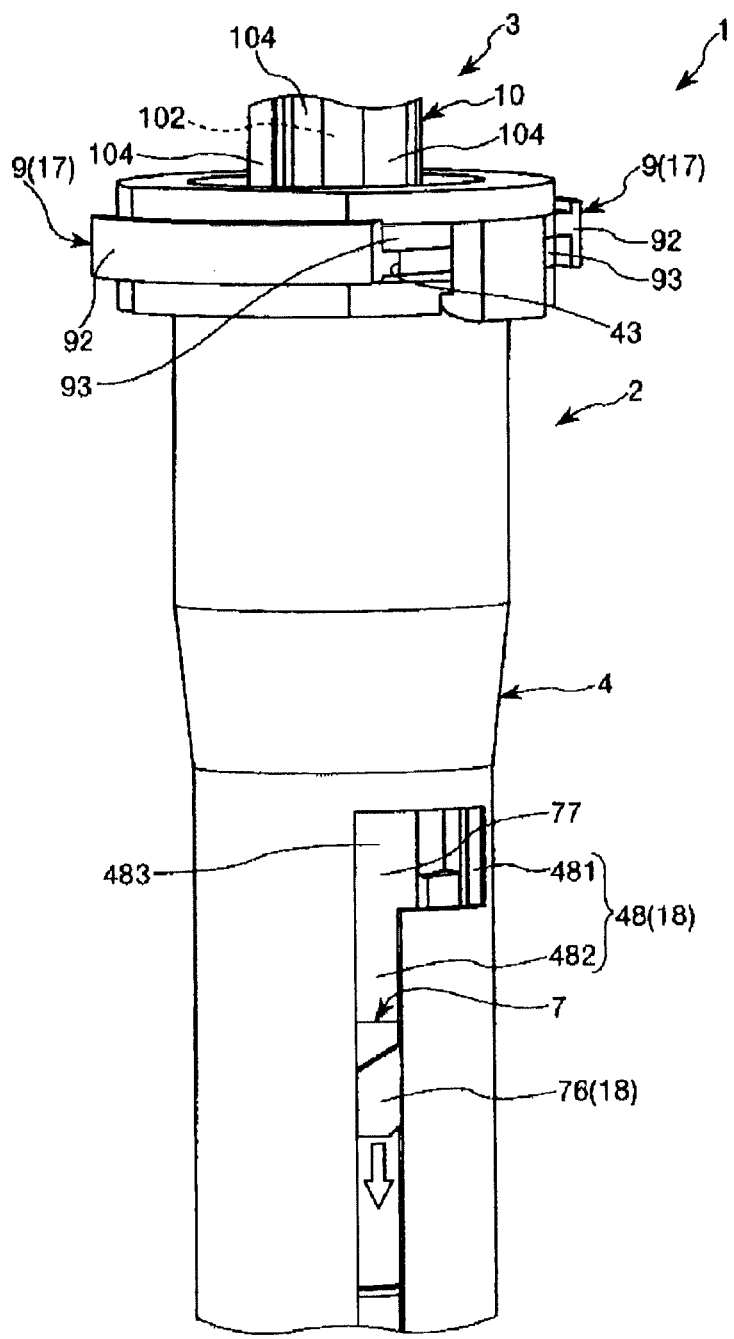
FIG. 9 is a perspective view (a view corresponding to FIG. 5) showing the process in which the first connector and the second connector of the connector assembly shown in FIG. 1 are brought into the assembled state.

When the second connector 3 is pushed down in the proximal end direction from the condition shown in FIG. 8 against biasing force of the coil spring 8, the insertion operation is resumed, and the first connector 2 is brought into the third state shown in FIG. 9. Incidentally, as shown in FIG. 5, even in the third state, the close contact between the first sealing member 6 and the second sealing member 11 is maintained.

When the second connector 3 is withdrawn from the first connector 2 in the condition (assembled state) shown in FIG. 9 (this operation will hereinafter be referred to as the "withdrawing operation"), the inner tube 7 is moved in the distal end direction together with the second connector 3 in accordance with the biasing force of the coil spring 8, contrary to the above-mentioned, and the first connector 2 is brought into the second state shown in FIG. 8. In this second state, further movement of the projected part 76 of the inner tube 7 in the distal end direction is restricted. Thus, the withdrawing operation can be temporarily restricted.

Furthermore, when the inner tube 7 is rotated in the opposite direction to the above-mentioned direction from the second condition, the first connector 2 is put into the first state shown in FIG. 7. As a result, the locking state between the inner tube 7 and the second connector 3 by the locking means 19 is released, thereby enabling movement of only the second connector 3 in the distal end direction, so that the withdrawing operation can be resumed. When the withdrawing operation is resumed, the first connector 2 and the second connector 3 are again put into the disassembled state shown in FIG. 6.

Thus, in the connector assembly 1, restriction on the insertion operation, release of the restriction on the insertion operation, restriction on the withdrawing operation, and release of the restriction on the withdrawing operation are performed depending on the position of the projected part 76 of the inner tube 7 in the groove part 48 of the outer tube 4. Accordingly, it can be said that the projected part 76 of the inner tube 7 and the groove part 48 of the outer tube 4 jointly form "operation restricting means 18" for restricting these operations.

As shown in FIG. 2, the inner tube 7 is provided at a distal end portion thereof with a plurality of (four in this embodiment) engagement pieces (elastic pieces) 77 projected in the distal end direction. Each of the engagement pieces 77 is provided at its distal end portion with a claw 771 capable of engaging with a recess (engagement section) 101a of the second connector 3.

Incidentally, the recess 101a is formed in a ring-like shape at a distal end portion of an outer peripheral portion 101 of the second connector body 10 along the circumferential direction.

The engagement pieces 77 are inclined outwardly in the condition where the second connector 3 is not yet inserted in the first connector 2. This ensures that in the condition where the second connector 3 is inserted in the first connector 2, each of the engagement pieces 77 can be brought into a state of being separated from the recess 101a of the second connector 3 (the state shown in FIGS. 3 and 10) and a state of being engaged with the recess 101a by being pressed by pressing parts 471 of the outer tube 4 closer to the recess 101a (the state shown in FIGS. 4, 5 and 11). Thus, by this engagement, the inner tube 7 and the second connector 3 are assuredly locked to each other.

Incidentally, the pressing parts 471 are composed of a plurality of (four in this embodiment) ribs formed on the inner peripheral portion 47 of the outer tube 4 along the axial direction of the outer tube 4.

In addition, these pressing parts 471 are arranged at regular intervals along the circumferential direction of the outer tube 4. In the condition shown in FIG. 10, one engagement piece 77 is located between the adjacent pressing parts 471, and pressing of the engagement pieces 77 by the pressing parts 471 is not yet performed. In this instance, the first connector 2 is in the above-mentioned first state.

The engagement pieces 77 are arranged at regular intervals around the axis of the inner tube 7. When the inner tube 7 is rotated as above-mentioned from the condition shown in FIG. 10, each of the engagement pieces 77 climbs an inclined surface 472 of the pressing part 471, and then one pressing part 471 presses one engagement piece 77 against the elastic force of the engagement piece 77. This ensures that the four engagement pieces 77 engage evenly along the circumferential direction of the second connector 3, so that the inner tube 7 and the second connector 3 are locked to each other more reliably. In this instance, the first connector 2 is in the above-mentioned second state. The condition in which the pressing parts 471 are pressing the engagement pieces 77 is maintained even after the first connector 2 is put into the above-mentioned third state.

Thus, in the connector assembly 1, it can be said that the engagement pieces 77 of the inner tube 7, the pressing parts 471 of the outer tube 4 and the recess 101a of the second connector 3 jointly form the "locking means 19" for locking the inner tube 7 and the second connector 3 to each other reliably. This locking means 19 operates when the first connector 2 is transferred from the first state into the second state, in other words, in conjunction with the releasing operation for releasing the restriction on the insertion operation. In addition, the locking means 19 operates also when, on the contrary to the above, the first connector 2 is transferred from the second state into the first state. In other words, the locking means 19 operates also in conjunction with the releasing operation for releasing the restriction on the withdrawing operation. This ensures that the close contact (liquid-tightness) between the first sealing member 6 and the second sealing member 11 can be reliably maintained during displacement of the first connector 2 between the first state and the second state, in other words, before and after the puncturing of the first sealing member 6 and the second sealing member 11 by the hollow needle 5. In addition, unexpected withdrawal (slipping off) of only the second connector 3 can be prevented at the time of withdrawal.

Incidentally, the materials for the outer tube 4, the inner tube 7, and the clamping members 9 are not particularly limited. Examples of the materials include various resins such as polyvinyl chloride, polyethylene, polypropylene, cyclic polyolefin, polystyrene, poly(4-methylpentene-1), polycarbonates, acrylic resins, acrylonitrile-butadiene-styrene copolymer, polyesters such as polyethylene terephthalate and polyethylene naphthalate, butadiene-styrene copolymer, and polyamides (e.g., nylon 6, nylon 6·6, nylon 6·10, nylon 12). Among these resins, such resins as polypropylene, cyclic polyolefin and polyesters are preferred, from the viewpoint of their high moldability and low water vapor permeability.

As shown in FIG. 2, the hollow needle 5 formed from a metallic material is disposed on the axis of the outer tube 4. As above-mentioned, the hollow needle 5 is supported at its proximal end portion by the hub part 42 of the outer tube 4.

The hollow needle 5 is tubular in shape, and its inner cavity functions as the first passage 52 permitting the dissolving liquid P (liquid) to pass therethrough. In addition, the hollow needle 5 has its distal end closed, and is formed with a side hole (opening part) 53 opening at a distal end portion of the wall part thereof. The side hole 53 communicates with the first passage 52.

The hollow needle 5 is formed at its distal end with a sharp needle point 51. As shown in FIG. 5, the first sealing member 6 of the first connector 2 and the second sealing member 11 of the second connector 3 to be described later can be punctured by the needle point 51. As shown in FIG. 5, in the assembled state, a portion of the hollow needle 5 from the needle point 51 to a part where the side hole 53 is formed is exposed (projected) into the inner cavity of the second connector 3. As a result, the inner cavity of the hollow needle 5 and the inner cavity of the second connector 3 communicate with each other through the side hole 53 of the hollow needle 5, in other words, the first passage 52 in the first connector 2 and a second passage 102 in the second connector 3 to be described later communicate with each other through the side hole 53 of the hollow needle 5.

As shown in FIG. 2, the first sealing member 6 is disposed inside the inner tube 7. The first sealing member 6 seals the inner cavity section of the inner tube 7, and the first sealing member 6 is disk-like in shape, and is disposed such that its thickness direction coincides with the axial direction of the inner tube 7. This ensures that the first sealing member 6 is easily and assuredly punctured by the needle point 51 of the hollow needle 5 when moved toward the proximal end side along the axial direction of the hollow needle 5.

In addition, the first sealing member 6 is an elastic body which is thicker at its central portion than at its edge portion. The central portion forms the first puncture section 61 to be punctured by the hollow needle 5. Further, the edge portion of the first sealing member 6 is sandwiched between the pair of plate-shaped sections 731, 732 of the inner tube 7 as above-mentioned. This ensures that the first sealing member 6 is assuredly fixed to the inner tube 7, and can be moved together with the inner tube 7.

In addition, in the connector assembly 1, the sum of the sliding resistance between portions of the first sealing member 6 (first puncture section 61) and the second sealing member 11 (second puncture section 111) that are punctured by the hollow needle 5 and the outer peripheral portion 54 of the hollow needle 5 that makes contact with the portions, and the sliding resistance between the reduced diameter part 741 of the sliding member 74 and the outer peripheral portion 54 of the hollow needle 5 making contact therewith, is set to be smaller than the biasing force of the coil spring 8. This ensures that when the first connector 2 releases the stopper 17 being in the third state shown in FIG. 5, the first connector 2 can be returned into the second state shown in FIG. 4 by the biasing force of the coil spring 8. Incidentally, the way of setting the magnitude relationship between the above forces is not particularly limited. Examples of the way of setting include: selection of the materials for the first sealing member 6, the second sealing member 11 and the sliding member 74; adjustment of the thicknesses of the first puncture section 61 and the second puncture section 111; selection of the material for the coil spring 8; adjustment of the wire diameter and the number of turns of the coil spring 8; adjustment of the outside diameter of the hollow needle 5; etc.

As shown in FIG. 2, the first puncture section 61 has its distal end surface 612 protuberant in a natural state in which no external force is exerted thereon. As shown in FIG. 3, in a close contact state where the first sealing member 6 and the second sealing member 11 are in close contact with each other, the protuberant distal end surface 612 is flattened. This ensures a more reliable close contact state, so that liquid-tightness can be secured at the boundary between the first sealing member 6 and the second sealing member 11. Consequently, transfer of the liquid in the assembled state can be performed safely and assuredly.

Incidentally, the material for the first sealing member 6 is not specifically restricted; for instance, the same materials as those mentioned above as examples of the material for the sliding member 74 can be used.

As shown in FIG. 2, the coil spring 8 made of a metallic material such as stainless steel is disposed inside the outer tube 4. In a compressed state, the distal end of the coil spring 8 abuts on the plate-shaped section 732 of the inner tube 7 and the proximal end thereof abuts on the bottom section 41 of the outer tube 4. This ensures that the first sealing member 6 can be assuredly biased in the distal end direction through the inner tube 7. Incidentally, the biasing means is not limited to the coil spring 8 but may be composed of a bellows-like leaf spring or a hollow cylindrical or bellows-like rubber.

As shown in FIGS. 1 and 2, the second connector 3 includes the tubular second connector body 10 and the second sealing member 11 provided on the second connector body 10.

The second connector body 10 is a hollow cylindrical member. The inner cavity of the second connector body 10 functions as a second passage 102 permitting a liquid to pass therethrough. As shown in FIG. 13, the second connector body 10 has its proximal end portion (second connection section) as the bottle needle section 103 having a tapered shape, so as to be able to puncture the rubber plug 505 of the bag 50. In addition, the bottle needle section 103 is formed with a side hole (not shown) therein. When the bottle needle section 103 is made to puncture the rubber plug 505 of the bag 50 so that the side hole is exposed to the inside of the bag 50, the inside of the bag 50 and the second passage 102 communicate with each other. As a result, the liquid passing through the second passage 102 can be supplied into the bag 50.

In addition, as above-mentioned, the second connector body 10 is formed at its intermediate portions with the engagement sections 105a, 105b for engagement with the first engagement section 91 of the first connector 2.

In addition, the second connector body 10 is formed on the outer peripheral portion thereof with a plurality of (four in this embodiment) ribs 104 along the longitudinal direction thereof. These ribs 104 are arranged at regular intervals along the circumferential direction of the outer peripheral portion of the second connector body 10. This enables reinforcement of the second connector body 10.

The second connector body 10 has, at its distal end portion, a sealing member mounting section 106 where to mount the second sealing member 11. The sealing member mounting section 106 is composed of a pair of annular plate-shaped sections 106a and 106b which vertically sandwich the second sealing member 11 therebetween.

Incidentally, the material for the second connector body 10 is not particularly limited. For example, such materials as mentioned above in the description of the outer tube 4, the inner tube 7 and the clamping members 9 of the first connector 2 can be used.

As shown in FIG. 2, the second sealing member 11 seals the inner cavity of the second connector body 10, and the second sealing member 11 is disk-like in shape, and is disposed such that its thickness direction coincides with the axial direction of the second connector body 10. This ensures that the second sealing member 11, together with the first sealing member 6 in close contact therewith, can be easily and reliably punctured by the needle point 51 of the hollow needle 5.

In addition, the second sealing member 11 is an elastic body which is thicker at its central portion than at its edge portion. The central portion forms the second puncture section 111 to be punctured by the hollow needle 5. Besides, the edge portion of the second sealing member 11 is clamped between the pair of plate-shaped sections 106a, 106b of the second connector body 10, as above-mentioned. As a result, the second sealing member 11 is reliably fixed to the second connector body 10.

As shown in FIG. 2, the second puncture section 111 has its proximal end surface 112 protuberant in a natural state in which no external force is exerted thereon. As shown in FIG. 3, in a close contact state where the first sealing member 6 and the second sealing member 11 are in close contact with each other, the protuberant proximal end surface 112 is flattened, like the distal end surface 612 of the first sealing member 6. This ensures a more reliable close contact state, so that liquid-tightness can be secured at the boundary between the first sealing member 6 and the second sealing member 11.

Incidentally, the material for the second sealing member 11 is not particularly limited. For example, the same materials as those mentioned above as examples of the material for the sliding member 74 may be used.

Now, operating states of the connector assembly 1 in use thereof will be described below.

[1] Process from disassembled state to assembled state (see the accompanying drawings in the order of FIG. 2 (FIG. 6)→FIG. 3 (FIG. 7)→FIG. 4 (FIG. 8)→FIG. 5 (FIG. 9))

The first connector 2 is mounted to the syringe 20. The second connector 3 is mounted to the bag 50.

As shown in FIG. 2, the second connector 3 in a disassembled state is moved from its proximal end side closer to a distal end portion of the first connector 2. In the disassembled state, the first connector 2 is in the first state (the state in which the projected part 76 of the inner tube 7 is located in the transverse groove 481 of the groove part 48 of the outer tube 4) (see FIG. 6). In addition, the first sealing member 6 is located on the distal end side relative to the hollow needle 5.

As shown in FIGS. 3 and 7, as the second connector 3 is inserted into the first connector 2, first, the distal end surface 612 of the first sealing member 6 of the first connector 2 and the proximal end surface 112 of the second sealing member 11 of the second connector 3 abut on each other, and are elastically deformed to make close contact with each other. In this instance, the first connector 2 is in the first state (see FIG. 7) as above-mentioned, so that the insertion operation of inserting the second connector 3 into the first connector 2 is temporarily restricted.

In addition, as shown in FIG. 3, the stopper 17 operates (the clamping members 9 of the first connector 2 engage with the engagement section 105a of the second connector 3) so that the second connector 3 is prevented from being moved back again in the distal end direction to be disengaged from the first connector 2.

Next, as shown in FIG. 8, when the inner tube 7 of the first connector 2 is rotated in the direction of arrow in the drawing, the first connector 2 is put into the second state (the state in which the projected part 76 of the inner tube 7 is located at the intersection part 483 of the groove part 48 of the outer tube 4). Then, the restriction on the insertion operation is released and the insertion operation can be resumed, as above-mentioned.

In addition, the assembled state of the first connector 2 and the second connector 3 is maintained by the stopper 17 and the locking means 19. Thus, withdrawal of the second connector 3 from the first connector 2, in other words, unwilling disassembly of the connector assembly 1 being in the assembled state, can be prevented. Accordingly, the dissolving liquid P can be safely transferred through the connector assembly 1.

Further, in the assembled state, the close contact between the first sealing member 6 of the first connector 2 and the second sealing member 11 of the second connector 3 is maintained (see FIG. 5). As a result, the liquid-tightness (airtightness) of the first passage 52 and the second passage 102, particularly in the vicinity of the joint therebetween, can be maintained reliably. Accordingly, the dissolving liquid P passing through these passages is securely prevented from leaking out of the connector assembly 1 in the assembled state.

In addition, in the condition shown in FIG. 5, the proximal end 78 of the inner tube 7 abuts on the distal end 412 of a wall part 411 vertically arranged from the bottom section 41 of the outer tube 4. As a result, the limit of insertion of the second connector 3 is regulated.

[2] Process from assembled state to disassembled state again (see the drawings in the order of FIG. 5 (FIG. 9)→FIG. 4 (FIG. 8)→FIG. 3 (FIG. 7)→FIG. 2 (FIG. 6))

Starting from the condition shown in FIGS. 5 and 9, the clamping members 9 are operated to release the first connector 2 and the second connector 3 from the locked state. This ensures that the withdrawing operation of withdrawing the second connector 3 from the first connector 2 can be started.

When the withdrawing operation is started, as shown in FIGS. 4 and 8, the second connector 3 is moved in the distal end direction, contrary to the above-mentioned. In this instance, the biasing force of the coil spring 8 is acting on the first sealing member 6 through the inner tube 7, so that the first sealing member 6 can follow up the movement of the second connector 3. Consequently, the close contact state of the first sealing member 6 and the second sealing member 11 is maintained also when the withdrawing operation is carried out.

Then, when the first connector 2 is brought into the second state, the withdrawing operation is temporarily restricted, as above-mentioned (see FIG. 8). In this instance, as shown in FIG. 4, in the hollow needle 5, its side hole 53 is located on the proximal end side relative to the second sealing member 11 (in the constitution shown in the drawing, relative to the first sealing member 6 located closer to the proximal end side than the second sealing member 11). Incidentally, in each of the first sealing member 6 and the second sealing member 11, the part punctured by the hollow needle 5 is closed by a self-closing property thereof.

Next, when the inner tube 7 is rotated in the direction opposite to the above-mentioned direction, the first connector 2 is put into the first state shown in FIG. 7. In this instance, as shown in FIG. 3, the locked state of the inner tube 7 and the second connector 3 by the locking means 19 is released, whereby movement of only the second connector 3 in the distal end direction is enabled. As a result, the withdrawing operation of withdrawing the second connector 3 can be resumed.

As shown in FIGS. 2 and 6, when the withdrawing operation is resumed, the first puncture section 61 and the second puncture section 111 in the close contact state are separated away from each other, so that the connector assembly 1 in the assembled state can be brought into the disassembled state again. Thereafter, it is possible to detach the first connector 2 from the syringe 20 and administer the liquid medical agent from the syringe 20.

Thus, in the connector assembly 1, in withdrawing the second connector 3 from the first connector 2, the first sealing member 6 and the second sealing member 11 can be prevented from being separated away from each other before the hollow needle 5 is completely disengaged from the second sealing member 11. This ensures that the liquid-tightness of the first passage 52 and the second passage 102 is maintained even during the disassembly operation of the connector assembly 1 in the assembled state; accordingly, the liquid medical agent (liquid) in these passages is securely prevented from leaking out of the connector assembly 1. Consequently, transfer of the liquid medical agent can be safely performed by use of the connector assembly 1.

While the connector assembly according to the present invention has been described above with reference to the embodiment shown in the drawings, the invention is not to be limited to the present embodiment. Each of the parts of the connector assembly can be replaced with a part of an arbitrary constitution that can exhibit the same function. Further, an arbitrary structural part may be added.

In addition, while the operation restricting means is composed of the groove part formed in the wall part of the outer tube and the projected part which projects from the wall part of the inner tube and which is inserted in the groove part, the present invention is not limited to this constitution. The operation restricting means may be composed of a groove part formed in the wall part of the inner tube and a projected part which projects from the wall part of the outer tube and which is inserted in the groove part.

Further, while the first puncture section and the second puncture section have had protuberant end surfaces, the present invention is not limited to this constitution. For example, only one of the end surfaces of these puncture sections may be protuberant.

INDUSTRIAL APPLICABILITY

The connector assembly according to the present invention includes a first connector and a second connector for being inserted in the first connector. The first connector includes a tubular first connector body provided at a distal end thereof with an opening for insertion of the second connector and at a proximal end thereof with a first connection section for connection with a first medical instrument, a hollow needle provided in an inner cavity section of the first connector body so as to communicate with the first connection section and which is provided with an opening part opening at a distal end portion thereof, a first sealing member for sealing the inner cavity section of the first connector body and which is made of an elastic material, the first sealing member having a first puncture section capable of being punctured by the hollow needle, and a biasing member for biasing the first puncture section in a distal end direction. The second connector includes a tubular second connector body provided at a distal end thereof with a second connection section for connection with a second medical instrument, and a second sealing member for sealing an inner cavity section of the second connector body and which is made of an elastic material and provided at a proximal end of the second connector body, the second sealing member having a second puncture section which makes close contact with the first puncture section when the second connector is inserted in the first connector body. The first connector is provided with an operation restricting means which, when the second connector is inserted into the first connector, temporarily restricts the insertion operation and permits resumption of the insertion operation if the restriction is released, and which, when the second connector is withdrawn from the first connector, temporarily restricts the withdrawing operation and permits resumption of the withdrawing operation if the restriction is released. In the process of insertion of the second connector into the first connector, the insertion operation is temporarily restricted by the operation restricting means when the first puncture section and the second puncture section make close contact with each other, and, upon resumption of the insertion operation by releasing the restriction, the first puncture section and the second puncture section in the close contact state are pierced by the hollow needle, and the operating part of the hollow needle is located on the distal end side relative to the second puncture section and then exposed to the inside of the inner cavity section of the second connector body. In the process of withdrawal of the second connector from the first connector, the withdrawing operation is temporarily restricted by the operation restricting means when the opening part of the hollow needle is located on the proximal end side relative to the first puncture section in the close contact state, and, upon resumption of the withdrawing operation by releasing the restriction, the first puncture section and the second puncture section are separated away from each other.

In the assembled state of the first connector and the second connector, therefore, the inner cavity of the hollow needle of the first connector and the inner cavity of the second connector body of the second connector communicate with each other. Through the inner cavity of the hollow needle and the inner cavity of the second connector body thus communicating with each other, a liquid can be assuredly transferred from the first connector side to the second connector side or from the second connector side to the first connector side. In addition, in the assembled state, close contact between the first sealing member of the first connector and the second sealing member of the second connector is maintained. This ensures that liquid-tightness (air-tightness) of the inner cavity of the hollow needle and the inner cavity of the second connector body can be maintained reliably, so that the liquid passing through these inner cavities can be securely prevented from leaking out of the connector assembly in the assembled state.

Particularly, in the connector assembly, in the process of withdrawing the second connector from the first connector, the withdrawing operation can be temporarily restricted; further, until the restriction is achieved, the first sealing member of the first connector and the second sealing member of the second connector can be maintained in the close contact state by the locking means. This ensures that even during the withdrawal of the second connector from the first connector, the liquid-tightness of the inner cavity of the hollow needle and the inner cavity of the second connector body is maintained, and, therefore, the liquid in these inner cavities can be securely prevented from unwillingly leaking out of the connector assembly. Consequently, the transfer of the liquid and the withdrawal after the transfer can be carried out safely.

Accordingly, the connector assembly of the present invention has industrial applicability.

The invention claimed is:

1. A connector assembly comprising:
a first connector; and
a second connector for being inserted in the first connector,
the first connector including a tubular first connector body provided at a distal end thereof with an opening for insertion of the second connector and at a proximal end thereof with a first connection section for connection with a first medical instrument, a hollow needle provided in an inner cavity section of the first connector body so as to communicate with the first connection section and which is provided with an opening part opening at a distal end portion thereof, a first sealing member for sealing the inner cavity section of the first connector body and which is made of an elastic material, the first sealing member having a first puncture section capable of being punctured by the hollow needle, and a biasing member for biasing the first puncture section in a distal end direction, and
the second connector including a tubular second connector body provided at a distal end thereof with a second connection section for connection with a second medical instrument, and a second sealing member for sealing an inner cavity section of the second connector body and which is made of an elastic material and provided at a proximal end of the second connector body, the second sealing member having a second puncture section which makes close contact with the first puncture section when the second connector is inserted in the first connector body,
wherein the first connector is provided with operation restricting means which, when the second connector is inserted into the first connector, temporarily restricts the insertion operation and permits resumption of the insertion operation if the restriction is released, and which, when the second connector is withdrawn from the first connector, temporarily restricts the withdrawing operation and permits resumption of the withdrawing operation if the restriction is released;
in the process of insertion of the second connector into the first connector, the insertion operation is temporarily restricted by the operation restricting means when the first puncture section and the second puncture section make close contact with each other, and, upon resumption of the insertion operation by releasing a restricted state of the insertion operation by the operation restricting means, the first puncture section and the second puncture section in the close contact state are punctured by the hollow needle, and the opening part of the hollow needle is located on the distal end side relative to the second puncture section and then exposed to the inside of the inner cavity section of the second connector body; and in the process of withdrawal of the second connector from the first connector, the withdrawing operation is temporarily restricted by the operation restricting means when the opening part of the hollow needle is located on the proximal end side relative to the first puncture section in the close contact state, and, upon resumption of the withdrawing operation by releasing a restricted state of the withdrawing operation by the operation restricting means, the first puncture section and the second puncture section are separated away from each other, the connector assembly further comprising locking means for locking the close contact state of the first puncture section and the second puncture section in conjunction with a releasing operation for releasing the restricted state of the insertion operation by the operation restricting means, wherein the first connector body includes an outer tube, and an inner tube displaceably disposed inside the outer tube, the locking means includes a plurality of engagement pieces disposed on the inner tube around an axis of the inner tube and being elastic, a pressing part provided on the outer tube and operative to press the engagement pieces against elastic forces of the engagement pieces for displacing the engagement pieces inward in conjunction with the releasing operation, and an engagement section provided on the second connector body and operative to engage with each of the engagement pieces when each of the engagement pieces is pressed by the pressing part, and wherein the first connector body is provided with a releasable stopper for restricting movement of the second connector body in the distal end direction in conjunction with the insertion operation in a state where the opening part of the hollow needle is located on the distal end side relative to the second puncture section and exposed to the inside of the inner cavity section of the second connector body.

2. The connector assembly according to claim 1, wherein the first connector has a biasing member for biasing the first puncture section in a distal end direction.

3. The connector assembly according to claim 1, wherein the operation restricting means includes a groove part which has a transverse groove formed in a wall part of one of the outer tube and the inner tube along a circumferential direction of the wall part and a longitudinal groove formed in the wall part along an axial direction of the wall part and communicating with the transverse groove, and a projected section which projects from a wall part of the other of the outer tube and the inner tube so as to be inserted in the groove part and which is moved in the groove part in accordance with displacement of the inner tube, and restriction on the insertion operation and release of the restricted state of the insertion operation by the operation restricting means and restriction on the withdrawing operation and release of the restricted state of the withdrawing operation by the operation restricting means can be performed depending on a position of the projected section in the groove part.

4. The connector assembly according to claim 1, wherein the stopper includes a first engagement section provided on an outer tube, an elastic section for biasing the first engagement section toward the inside of the outer tube, and a plurality of second engagement sections which are provided on the second connector body and which engage with the first engagement section depending on depth of insertion of the second connector body into the first connector.

5. The connector assembly according to claim 1, wherein the release of the restricted state of the insertion operation by the operation restricting means and the release of the restricted state of the withdrawing operation by the operation restricting means are performed by relative rotation of the first connector and the second connector around an axis of the first connector and the second connector, and, at that time, the first puncture section and the second puncture section are rotated in the same direction.

6. The connector assembly according to claim 1,
wherein the first medical instrument has a syringe outer tube; and
in the first connector, the first connection section thereof is connected to a spout of the syringe outer tube.

7. The connector assembly according to claim 1,
wherein the second medical instrument has a liquid container capable of containing a liquid therein; and
in the second connector, the second connection section thereof is connected to a mouth part of the liquid container.

* * * * *